United States Patent [19]

Koller et al.

[11] Patent Number: 4,852,550

[45] Date of Patent: Aug. 1, 1989

[54] INSTRUMENT FOR INSERTION INTO AN ENDOSCOPE SHAFT

[75] Inventors: Roland Koller, Öhningen; Horst Dittrich, Immendingen, both of Fed. Rep. of Germany

[73] Assignee: Karl Storz GmbH & Co., Tuttlingen, Fed. Rep. of Germany

[21] Appl. No.: 187,426

[22] Filed: Apr. 28, 1988

[30] Foreign Application Priority Data

Apr. 28, 1987 [DE] Fed. Rep. of Germany ....... 3714170

[51] Int. Cl.[4] .............................................. A61B 1/00
[52] U.S. Cl. ......................................................... 128/4
[58] Field of Search ....................................... 128/4, 6

[56] References Cited

U.S. PATENT DOCUMENTS

| 3,144,020 | 8/1964 | Zingale | 128/4 |
| 3,791,379 | 2/1974 | Storz | 128/4 |
| 4,211,215 | 7/1980 | Heine et al. | 128/4 |
| 4,430,996 | 2/1984 | Bonnet | 128/4 X |

Primary Examiner—William H. Grieb
Attorney, Agent, or Firm—Barnes & Thornburg

[57] ABSTRACT

An insertion assembly is provided for controlling insertion of an instrument assembly into an endoscope shaft. Instrument locking elements are provided having a first position preventing movement of the instrument assembly relative to the shaft and having a second position allowing movement of the instrument assembly relative to the shaft. Actuator locking elements are provided having a first position allowing bending of the instrument assembly and having a second position preventing bending of the instrument assembly. Movement of the instrument locking elements into the first position moves the actuator locking elements into the first position. Further, movement of the instrument locking elements into the second position moves the actuator locking elements into the second position.

15 Claims, 2 Drawing Sheets

INSTRUMENT FOR INSERTION INTO AN ENDOSCOPE SHAFT

BACKGROUND AND SUMMARY OF THE INVENTION

The present invention relates to an assembly controlling the insertion and movement of an instrument assembly.

Such instruments may be, for instance, obturators and are frequently employed in many ways in endoscopic examinations and treatments.

In a number of endoscopic examinations and treatments, endoscopic shafts are required which are provided with an insulation from the inserted instrument. The insulation can be in the form of a small tube or tubelet. For reasons of sterilization, thermal resistance, etc., it is advantageous for this insulating tubelet to be made of a ceramic material. It has turned out, however, that ceramic material tends to crack and break during work with the endoscopic shafts for reasons which could be explained in very rare cases only. A more detailed explanation is not necessary of the fact that such cracking and breaking of the ceramic material is extremely bothering, for instance, when this happens during an endoscopic examination of the knee or in similar operations. Thus, in spite of the foregoing disadvantages, plastic tubelets have been commonly used as insulation material.

It is thus an object of the present invention to provide an assembly which permits the use of a protective ceramic tubelet or protective coating of ceramic material on the interior shaft without cracking or breaking when used with an instrument assembly inserted into the shaft. It is a further object to provide such a ceramic tubelet or ceramic material protection to a shaft, such that there will be no interference to the normal operation of the instrument assembly inserted into the shaft.

These objects and other objects are achieved by providing an insertion assembly for Controlling the insertion and movement of an instrument assembly in a shaft in which the instrument assembly is of the type bendable by an actuator device. Instrument locking elements are provided which prevent movement or allow movement of the instrument assembly relative to the shaft according to a given position of the instrument locking elements. Actuator locking elements are provided which are movable between a position allowing bending of the instrument assembly and preventing bending of the instrument assembly. When the instrument locking elements prevent movement of the instrument assembly relative to the shaft, the actuator locking elements allow bending of the instrument assembly by the actuator device. When the instrument locking elements are moved into the position permitting movement of the instrument assembly relative to the shaft, the actuator locking elements prevent bending of the instrument assembly.

According to the present invention, it was found that the main reason of cracking and breaking of the ceramic material used for insulating tubelets occurred during the insertion of the instrument assembly through the shaft, during removal of the instrument assembly through the shaft, or whenever the instrument assembly was moved with respect to the shaft. Once the instrument assembly is in place in the shaft, the normal operation of the instrument assembly, such as during bending, was found not to cause cracking of the ceramic material. It was found that when the actuator device bent the instrument assembly during movement of the instrument assembly relative to the shaft, the bent portion of the instrument assembly pressed against the ceramic material and thus caused the insulation to crack and break.

The present invention provides a system in which the actuator device will be prevented from bending the instrument assembly when the instrument assembly is allowed to move relative to the shaft. However, when the instrument assembly is prevented from moving relative to the shaft, the actuator device will be permitted to bend the instrument assembly. Thus, during movement of the instrument with respect to the shaft, the instrument assembly cannot be bent and thus cannot cause the cracking and breaking previously experienced when the assembly was bent during movement relative to the shaft. Further, once the instrument assembly is prevented from moving relative to the shaft, such as when normal operation of the bending of the instrument assembly is desired, the actuator element will be permitted to bend the instrument assembly.

According to advantageous features of certain preferred embodiments of the invention, the instrument locking elements include a locking ring which is rotatable between a first position in which the instrument assembly is locked relative to the shaft and a second position in which the instrument assembly is unlocked relative to the shaft. In certain preferred embodiments, the actuator locking elements are moved into a first position, allowing bending of the instrument assembly when the locking ring is moved into the first position, preventing movement of the instrument assembly relative to the shaft. Further, the actuator locking elements are moved into a second position, preventing bending of the instrument assembly when the locking ring is moved into the second position, allowing relative movement between the instrument assembly and the shaft. Thus, without any additional operation being required, the instrument assembly cannot be moved relative to the shaft with the front section being bent off, since when relative movement of the instrument assembly and the shaft is allowed, the actuator device will automatically be prevented from bending the instrument assembly.

It is also contemplated to use a basic inventive idea underlying the invention, i.e., the idea of employing the rotation of an insertion locking ring for locking or release of an actuator element as well, for instruments in which the front section of an instrument is bent by means of an electromagnetic mechanism, in which the actuator element merely controls the excitation by electric current.

It is further contemplated to use the present invention for instruments in which a mechanism is provided to transfer the motion from the actuator element to the front section of an instrument. In certain preferred embodiments, this mechanism includes a guiding element having an actuating rod element slidingly disposed therein. Further, a stationary supporting element is fixedly attached to the guiding element The stationary supporting element and the actuating rod element are fixedly attached to a front section of the instrument assembly. The actuating rod element can be moved back and forth with respect to the guiding element, thereby providing bending of the front section of the instrument.

According to other advantageous features of certain preferred embodiments of the invention, a locking ring is provided with an inner circumference which surrounds the guiding element. A pin element is disposed in the guiding element in between the actuator rod element and the inner circumference of the locking ring. In one position, the inner circumference of the locking ring locks the pin in between the locking ring and the actuator rod element, thereby preventing bending. In another position, the pin is not locked between the actuator rod element and the locking ring, thereby allowing bending.

In certain preferred embodiments, the inner circumference of the locking ring includes a contour service such that upon rotation of the locking ring into one position, the contour moves toward the actuator rod element, thereby locking the pin between the actuator rod element and the inner circumference of the locking ring. As the locking ring is rotated out of this position, the contour surface moves away from the actuator rod element, thereby unlocking the pin element from the actuator rod element.

According to other advantageous features of certain preferred embodiments of the invention, a spring element is provided for biasing the pin against the inner circumference of the locking ring. In certain other embodiments, a ball-shaped element is disposed between the pin element and the inner circumference of the locking ring. In other preferred embodiments, an actuator rod spring element is provided for biasing the actuator rod element into a position such that the instrument assembly is unbent. All of these features enhance the operational reliability of the present invention.

According to other advantageous features of certain preferred embodiments, the instrument assembly used includes a rigid bevelled region immediately proceeding the bendable front section. The rigid bevelled region is disposed on each side towards which the front section is bent. In these embodiments, a force introduced into the instrument, as it may arise in the bending operation, will be precluded from creating another cause of destruction of a shaft insulated with ceramic material. In conventional instruments, without this bevelled region, the force introduced upon bending may cause parts of the instrument to bear against the ceramic shaft.

Other objects, advantages and novel features of the present invention will become apparent from the following detailed description of the invention when considered in conjunction with the accompanying drawings.

DETAILED DESCRIPTION OF THE DRAWINGS

Figure 1:
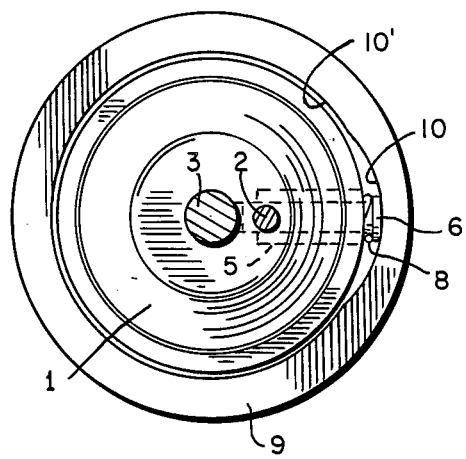
FIG. 1 is a plan view of one part of an instrument according to the present invention.
Figure 2:
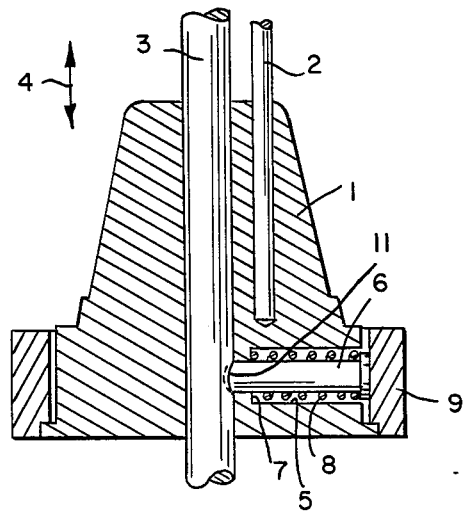
FIG. 2 is a cross-sectional side view of an instrument according to the present invention.
Figure 4:
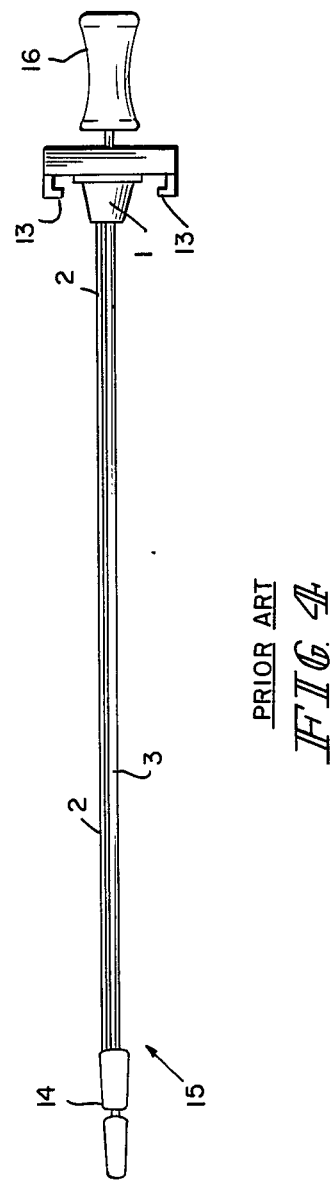
FIG. 4 is a plan view of a bendable front section of an instrument assembly.

In the drawing figures, reference numeral 1 denotes a guide element for a supporting bar 2 and a push rod 3. The supporting bar 2 and the push rod 3 are fixedly attached to a bendable front section 14 of an instrument assembly, generally at 15, as shown in FIG. 4. This instrument assembly 15 is disposed above the guide element 1 as shown in FIG. 2. The push rod 3 is slidably movable with respect to the guide element 1, as shown by arrow 4 in FIG. 2. The supporting bar 2 is fixedly attached to the guide element 1. An actuator element 16, which is shown in FIG. 4, is provided outside the assembly 15 to affect the sliding movement of the push rod 3. By sliding the push rod 3, the front section 14 can be bent. Thus, the sliding push rod 3 and the supporting bar 2 transfer motion into the bending movement of the front section 14.

A transverse bore 5 is also provided in the guide element 1. A locking pin 6 is inserted into the transverse bore 5. A locking ring 9 surrounds the guide element 1 and the pin 6. The locking ring 9 has an inner circumference facing the guide element 1 and the pin 6. A spring 8 is provided which biases the locking pin 6 in the direction toward the locking ring 9. The spring 8 is supported on a shoulder 7.

Figure 3:
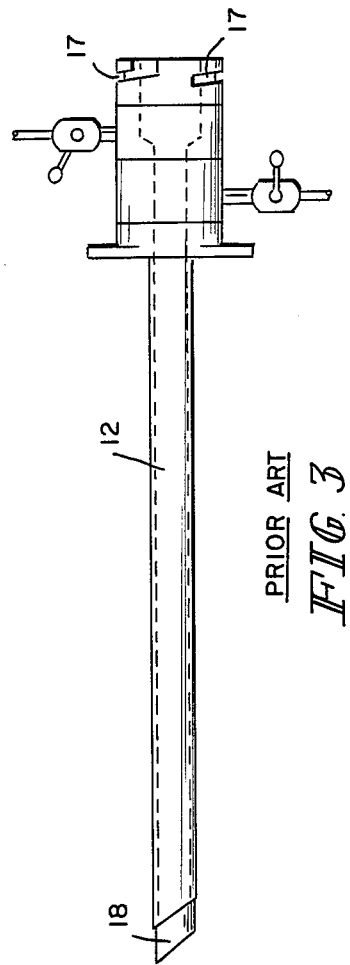
FIG. 3 is a plan view of an endoscopic shaft.

The locking ring 9 is provided for locking of the instrument assembly 15 relative to an endoscopic shaft 12 after insertion into the shaft 12. The endoscopic shaft is illustrated in FIG. 3. In certain embodiments, the locking ring 9 is provided with bayonet elements 13 as shown in FIG. 4 to provide for locking to the shaft 12. Locking rings that only provide locking of an instrument relative to a shaft are known in the endoscope related area of technology.

The inside shape of the locking ring 9 (the inner circumference) includes a contour 10, 10' including a camming arrangement having a pin-locking contour surface 10' and an area 10 recessed away from the guide element 1 for unlocking the locking pin 6. When the locking pin bears against the pin-locking contour 10' of the locking ring 9, the locking pin 6 is displaced against the force of spring 8 in a direction toward the push rod 3. The locking pin 6 engages into a recess 11 in the push rod 3, and thus locks the movement of the push rod 3 in the direction of arrow 4. Thus, the front section 14 cannot be bent. The locking ring 9 in this position allows relative movement between the instrument assembly 15 and the shaft 12.

However, when the locking pin 6, under the bias of spring 8, bears against the recessed contour area 10 of the locking ring 9, the locking pin 6 is withdrawn and does not engage into the recess 11 in the push rod 3. Thus, the push rod 3 is released and can be moved in the direction of arrow 4 by the actuator element, thereby providing the capability of bending the front section 14. The locking ring 9 in this position prevents relative movement between the instrument assembly 15 and the shaft 12.

The angular position of the pin-unlocking, recessed, contour area 10 in relation to the locking ring bayonet element (not shown), which are provided to lock the ring in an endoscopic shaft, is so calculated that the locking pin 6 will bear against the recessed contour 10 thereby unlocking the locking pin 6 only when the instrument is properly locked into the shaft.

The present invention assembly thus entails a number of advantages as discussed below.

When the locking ring 9 is in the instrument-releasing position in which the instrument 15 can be withdrawn from the shaft 12, the locking pin 6 bears against the pin-locking contour 10' so that bending of the front section 14 is prevented. Thus, the instrument 15 may be withdrawn from the shaft 12 only with the front section 14 in a straight position such that damage to sensitive inserts 18 in the shaft 12 will be precluded. Since the locking ring 9 will not be rotated before the next insertion after removal, the push rod 3 and thus the front section 14, remain in the locked condition so that the operation of insertion will be carried out with the front section 14 in the straight position, even if the actuator element 16 which is used to bend the front section 14 is inadvertently touched. Only in the position where the instrument 15 is locked relative to the shaft 12, will the push rod 3 be released so that the front section 14 can be bent.

As the locking of the instrument 15 in the shaft 12 is an indispensable operation, the inventive safety measure according to the present invention does not require any additional operations, and specifically does not require additional operations which an operator may forget which would render the success of treatment doubtful.

Even though the invention has been described in the foregoing with reference to a specific embodiment this description does not limit the scope of the invention in any way.

For example, it is contemplated to interpose an additional ball between the locking pin and the locking ring and/or the push rod in order to achieve a "softer" operation.

It is also contemplated to provide an additional spring to bias the push rod and thus the bendable front section into a position in which the front section is "straight".

Moreover, to achieve a further safety measure against cracking and breaking of a ceramic tubelet, it is contemplated that the instrument be bevelled in the rigid zone immediately preceding the bendable front section on each side towards which bending takes place.

It is also contemplated to use the basic inventive ideas of the present invention in instruments where the bendable front section is actuated electrically rather than mechanically.

Further, it is contemplated that the endoscopic shaft into which the instrument is inserted may itself form part of another insert.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. Insertion assembly for controlling insertion of an instrument assembly into an endoscope shaft, said instrument assembly being of the type bendable by actuator means, comprising:
    instrument locking means having a first position for preventing movement of said instrument assembly relative to said shaft and having a second position allowing movement of said instrument assembly relative to said shaft, said instrument locking means being movable between said first and second positions;
    actuator locking means having a first position for allowing bending of said instrument assembly by said actuator means and having a second position for preventing said actuator means from bending said instrument assembly, said actuator locking means being movable between said first and second positions; and
    wherein movement of said instrument locking means into said first position moves said actuator locking means into said first position and wherein movement of said instrument locking means into said second position moves said actuator locking means into said second position.

2. Insertion assembly as in claim 1, wherein said instrument locking means comprise a locking ring, said ring being rotatable between said first position and said second position.

3. Insertion assembly as in claim 2, wherein said actuator locking means are movable between said first position and said second position in response to rotation of said locking ring between said first position and said second position.

4. Insertion assembly as in claim 3, further including guiding means;
    actuating rod means slidably disposed in said guiding means and fixedly attached to a front section of said instrument assembly for facilitating bending of said front section of said instrument assembly, said actuating rod means being movable by said actuator means; and
    stationary supporting means fixedly attached to said guiding means and fixedly attached to said front section of said instrument assembly for facilitating bending of said front section of said instrument assembly.

5. Instrument assembly as in claim 4, wherein said locking ring includes an inner circumference surrounding said guiding means, said actuator locking means including a pin means slidingly disposed in said guiding means between said actuator rod means and said inner circumference of said locking ring, said pin means being locked between said inner circumference of said locking ring and said actuator rod means in said second position of said locking ring thereby preventing bending of said instrument assembly, and said pin means being unlocked between said inner circumference of said locking ring and said actuator rod means in said first position, thereby allowing bending of said instrument assembly.

6. Insertion assembly as in claim 5, wherein said inner circumference of said locking ring includes a contour surface such that upon rotation of said locking ring into said second position, said contour surface moves toward said actuator rod means thereby locking said pin means into said actuator rod means and upon rotation of said locking ring into said first position, said contour surface moves away from said actuator rod means thereby unlocking said pin means from said actuator rod means.

7. Insertion assembly as in claim 6, wherein said actuator rod means includes a recess area into which said pin means engages in said second position.

8. Insertion assembly as in claim 7, wherein said guide means includes a bore substantially transverse to said actuator rod means, said pin means being disposed in said guide means bore.

9. Insertion assembly as in claim 7, further including spring means for biasing said pin means against said inner circumference of said locking ring.

10. Insertion assembly as in claim 9, further including ball-shaped means disposed between said pin means and said inner circumference of said locking ring.

11. Insertion assembly as in claim 9, further including an actuator rod spring means for biasing said actuator rod means into a position such that said instrument assembly is unbent.

12. Insertion assembly as in claim 4, wherein said stationary supporting means comprise a support bar.

13. Insertion assembly as in claim 4, further including at least a portion of said instrument assembly, said at least a portion of said instrument assembly having a rigid bevelled region immediately preceding said bendable front section of said instrument assembly, said rigid bevelled region being disposed on each side towards which said front section is bent.

14. Insertion assembly as in claim 4, further including at least a portion of said instrument assembly, said instrument assembly being an obturator used with a ceramic insulated shaft.

15. Insertion assembly for controlling insertion of an instrument assembly into an endoscope shaft, said instrument assembly being of the type bendable by actuator means, comprising:

instrument locking means having a first position for preventing movement of said instrument assembly relative to said shaft and having a second position allowing movement of said instrument assembly relative to said shaft, said instrument locking means being movable between said first and second positions;

actuator locking means having a first position for allowing bending of said instrument assembly by said actuator means and having a second position for preventing said actuator means from bending said instrument assembly, said actuator locking means being movable between said first and second positions; and controlling means for controlling said instrument locking means and said actuator locking means such that both said instrument locking means and said actuator locking means are each in one of said first position simultaneously and said second position simultaneously.

* * * * *